United States Patent
Chiarelli et al.

(10) Patent No.: US 8,758,804 B2
(45) Date of Patent: Jun. 24, 2014

(54) CONTROLLED AND CONTINUED DELIVERY OF RIFAXIMIN AND/OR OTHER SUBSTANCES

(75) Inventors: Piero Chiarelli, S. Giuliano Terme (IT); Renzo Dalseno, Milan (IT)

(73) Assignee: Fadim S.R.L., Desio (IT)

( * ) Notice: Subject to any disclaimer, the term of this patent is extended or adjusted under 35 U.S.C. 154(b) by 1499 days.

(21) Appl. No.: 10/533,768

(22) PCT Filed: Nov. 5, 2003

(86) PCT No.: PCT/EP03/12346
§ 371 (c)(1), (2), (4) Date: May 4, 2005

(87) PCT Pub. No.: WO2004/041240
PCT Pub. Date: May 21, 2004

(65) Prior Publication Data
US 2006/0110447 A1 May 25, 2006

(30) Foreign Application Priority Data

| Nov. 5, 2002 | (IT) | FI2002A0212 |
| Nov. 18, 2002 | (IT) | MI2002A2438 |
| Jan. 14, 2003 | (IT) | PI2003A0005 |
| Feb. 21, 2003 | (IT) | PI2003A0013 |

(51) Int. Cl.
*A61K 9/70* (2006.01)

(52) U.S. Cl.
USPC ........................................................ 424/443

(58) Field of Classification Search
None
See application file for complete search history.

(56) References Cited

U.S. PATENT DOCUMENTS

| 4,341,785 | A | | 7/1982 | Marchi et al. ................. 424/256 |
| 4,904,247 | A | * | 2/1990 | Therriault et al. ............ 604/304 |
| 4,908,213 | A | * | 3/1990 | Govil et al. ................... 424/447 |
| 5,674,346 | A | * | 10/1997 | Kundel ....................... 156/272.2 |
| 6,194,455 | B1 | * | 2/2001 | Wharton ....................... 514/532 |
| 2002/0004065 | A1 | * | 1/2002 | Kanios .......................... 424/449 |

FOREIGN PATENT DOCUMENTS

| EP | 0 547 294 | 6/1993 |
| FR | 6.300 | 9/1968 |
| WO | WO 96/40086 | 12/1996 |
| WO | WO 99/15210 | 4/1999 |

OTHER PUBLICATIONS

Gionchetti et al, Eur Rev Med Pharmacol Sci, 3, p. 27-30, 1999.*
Sinha et al. Drug Development and Industrial Pharmacy 26(11), 1131-1140, 2000.*
Hoover et al. Diagnostic microbiology and infectious diseas 16(2), p. 111-118, 1993.*

(Continued)

*Primary Examiner* — Nissa Westerberg
(74) *Attorney, Agent, or Firm* — Ohlandt Greeley Ruggiero & Perle L.L.P.

(57) ABSTRACT

A gum-like device is designed for the controlled and continued delivery of rifaximin, without producing the usually intense red coloration, for the resolution of the infections and the reduction of the inflammation in the oral cavity and in the laryngo-pharyngeal one. The device also protects either the gum or the dental apparatus from acute infections, from the infiltration and the stagnation of the food, and fights chronic infections such as in the periodontal pockets. Moreover, the device can be used to protect the gum from the traumatizing collision that the food exercises during the mastication.

16 Claims, 1 Drawing Sheet

(56) References Cited

OTHER PUBLICATIONS

Hoover, et al., "*Antimicrobial Activity and Spectrum of Rifaximin, a New Topical Rifamycin Derivative*", Diagn Microbiol Infect Dis, 1993;16:111-118.

Berlo, J.A. et al., "A Prospective Study in Healthy Volunteers of the Topical Absorption of a 5% Rifaximin Cream," *Bioscience Ediprint Inc.: Drugs Under Experimental and Clinical Research* vol. XX (5), pp. 205-508.

Committee for Veterinary Medicinal Products, "Rifaxmin (Extension to Topical Use) Summary Report (3)," *European Agency for the Evaluation of Medicinal Products*, May 1998, Document 443/98-Final, pp. 1-4.

Adachi, Javier A. et al., "Rifaximin: A Novel Nonabsorbed Rifamycin for Gastrointestinal Disorders," *Clinical Infectious Diseases*, Feb. 15, 2006; vol. 42, pp. 541-547.

Cottreau, Jessica et al., "Rifaximin: a nonsystemic rifamycin antibiotic for gastrointestinal infections" Abstract from *Expert Review of Anti-Infective Therapy*, vol. 8, No. 7, Jul. 2010, pp. 747-760, Abstract only.

Hoover, William W., et al. "Antimicronial Activity and Spectrum of Rifaximin, a New Topical Rifamycin Derivative," *Diagnostic Microbiology of Infectious Diseases*, 1993, vol. 16: pp. 111-118.

Merriam-Webster online dictionary: definitions of "local," "topical" and "transdermal" downloaded Jan. 5, 2011 from http://www.merriam-webster.com/dictionary.

Palazzini, E. et al., "Treatment of pyogenic skin infections with Rifaximin cream," *European Review for Medical and Pharmacological Sciences*, 1993, vol. XV, pp. 87-92.

Parini, Paolo et al., "Effects of rifaximin and paromomycin in the treatment of portal-systemic encephalopathy," Abstract, *Current Therapeutic Research*, vol. 52, Issue 1, Jul. 1992; pp. 34-39 (downloaded from www.sciencedirect.com).

Prasad, Errol S. et al., "In vitro Activity of Rifaxamin, a Topical Rifamycin Derivitive Against *Chlamydia trachomatis*," *Diagnostic Microbiology of Infectious Diseases*, 1993, vol. 16, pp. 135-136.

Scarpignato, Carmelo et al., "Rifaxamin, a Poorly Absorbed Antibiotic: Pharmacology and Clinical Potential," *Chemotherapy*, 2005, vol. 51 (Suppl 1), pp. 36-66.

Taylor, David N., "Rifaximin, a Nonabsorbed Oral Antibiotic, Prevents Shigellosis after Experimental Challenge," *Clinical Infectious Diseases*, 2006; vol. 42, pp. 1283-1288.

Venturini, A.P. et al., Transcutaneous Absorption of a Topical Rifamycin Preparation: Rifaximin (L/105), *Drugs Experimental Clinical Research*, 1987, vol. XIII No. 4, pp. 233-236.

Weinstock, Leonard B., "Irritable Bowel Syndrome: Emergence of New Diagnostic and Treatment Options," Paper developed Oct. 13, 2009 pp. 1-19, at Washington University School of Medicine, St.Louis, MO, unpublished, available at www.gidoctor.net.

\* cited by examiner

CONTROLLED AND CONTINUED DELIVERY OF RIFAXIMIN AND/OR OTHER SUBSTANCES

DISCUSSION OF THE BACKGROUND ART

The progress of the dental technique and the medical treatment of these last years has carried to excellent solutions for nearly the totality of dental pathologies regarding hard tissues such as tooth and bone, but not for periodontal tissue and gum, that also carry out an extremely important role in the conservation and good functionality of the masticator apparatus.

The periodontal tissue and the gum in particular assures to the system tooth-periodontal tissue-bone an essential protection from all those pathogenic and destabilizing agents that come from the oral cavity.

Moreover chronic infections in the oral cavity are absolute insensitive to systemic treatment by means of antibiotic. One of the scopes of present the invention is to supply adequate means for the protection of the masticator apparatus and drug delivery in the oral cavity, using material adapted for this purpose.

Rifaximin is known like a powerful and effective antibiotic to wide number of pathogenic agents. Its use is currently relegated to the treatment of the diarrheas and internal infections. One characteristic that renders precious such an antibiotic is that it does not permeate through the mucosae. This fact allows a local use of such an antibiotic at high concentrations, with a great efficacy, a null systemic concentration and therefore collateral effects. On the other hand, the rifaximin possesses a very low solubility in the physiological liquids. For this reasons it remains in form of small crystal, of intense red color, dispersed in the place of administration. For aesthetic reasons, this fact prevents its use in all those places, like the mouth, where the patient wishes to maintain a socially acceptable aspect. Moreover, the drug in the form of small crystals, generates a peaky of concentration, at the moment of the application but then it disperses itself quickly far away from the point where it is placed losing its effectiveness. In truth, a continuous and calibrated delivery along the time of rifaximin would be a very good tool for the treatment of a wide ensemble of gram-positive and gram-negative bacteria and it renders possible its use outside of the intestine.

An important class of materials is that one of the, so-called, bi-phasic materials. They are constituted from two phases: a solid one, made by an elastic matrix that maintains its own shape and is able to confer to the material a strong rubber-like elasticity, and a liquid part that fills up its pores that, in gels, are constituted by the molecular interstices. Their importance is given by the fact that the overwhelming majority of biological tissues, for instance, the cartilage, the derma, the endothelia, the tendons, the gray matter of the brain, the chromosomes and the several organelles of the cell are made up of bi-phasic materials. They can have a strong elasticity and can be resistant to repeated cycles of loading like tendons. The volume and the shape that a bi-phasic materials assume derive from the equilibrium of many forces; in exemplified way, it can be said that the fluid enters in the pores, or in the inter-molecular spaces of the solid matrix (polymer network), and swells it for an effect of "suction". This phenomenon is generated from the affinity (attractive force) existing between the molecules of the fluid and those of the solid matrix. The solid matrix (polymer networks) opposes itself to this swelling tendency till an equilibrium volume is reached.

Varying the affinity between the polymer network, constituting the solid matrix, and the fluid, the water content inside of a biphasic material can be regulated. Usually the ratio in weight between fluid (water) and solid part (polymer net) can arrive to advanced values also to 10. The present invention consists in having designed a new method and way of administration of the rifaximin dosed and continued in the time, by means of the formulation and realization of suited bi-phasic materials and devices that allow it.

By means of the devices, matter of this patent, the use of the rifaximin becomes possible outside the intestine (e.g., in the oral and pharyngeal or nasal cavity, in the rectum and vagina). In particular they allows high level, constant in time, of concentration of rifaximin in aqueous body fluids avoiding the intense red color that it produces in the neighboring of the place of administration.

SUMMARY OF THE INVENTION

In particular, the invention sees the employment of a solid and elastic matrix that contains an interstitial fluid. The material contains, together with the interstitial liquid, the medicinal one in crystals, that melting themselves into the interstitial liquid, gradually let antibiotic to diffuse outside. The material systems have been conceived, and this is one of the aspects of this invention, with the property to enhance the dissolution of rifaximin in the interstitial solution to a very high level.

Moreover, objects of the present invention consist also in the use of the mechanism of the fluid absorption (water) inside the biphasic materials, with the intent to regulate the delivery of the rifaximin.

DETAILED DESCRIPTION OF THE PREFERRED EMBODIMENT

Figure 1:
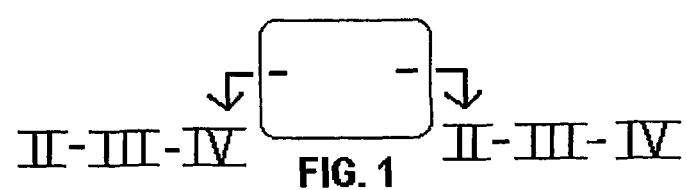
FIG. 1 depicts the device according to the present invention in the shape of a film.

Here, we make an example of a material synthesis even if, all poly-acid, poly-basic and poly-amphoteric polymers (for instance equipped of carboxylic and/or aminic groups) or hydrophilic ones like: poly-saccharides (xanthan, guar and similar), cellulose-derivatives, alkyl-cellulose, hydroxy-alchyl-cellulose, polyvinyl-sulfonates, poly-acrylates, poly-acrylammides and similar ones, polycarboxylates of vinyl and hydroxypropylmethyl-cellulose are equally useful for obtaining a bi-phasic material for controlled and continued delivery of rifaximin.

Example: hydrogel described in EP-A-0 058 497, as an example but not exclusively, poly-vinyl-alcohol (PVA) (of molecular weight preferably but not exclusively between 500.000 and 10.000) dissolved in water, preferably but not exclusively to a concentration of 10% in weight.

In this solution—but a procedure is also possible that does not preview it—it is added the poly-acrylic acid (preferably but not exclusively of a molecular weight between 4.000.000 and 500) up to a concentration, preferably but not exclusively, between 0.2% and 20% in weight. All those poly-acrylic polymers, as those ones commercially available under the trademark Carbopol and Carbomer must be considered equivalents to the poly-acrylic acid. In this solution jaluronic-acid—but a procedure is possible also that it does not preview it—(preferably but not exclusively of molecular weight between 4.000.000 and 100, and in a concentration between 0.5% and 20% in weight) can be added.

In this solution a bio-adhesive polymer (later on indicated more simply like adhesive) may be dissolved (but a procedure is possible also that it does not preview it), preferably but not exclusively: silicones polymers, poly-isobutylene, acrylic polymers, poly-oxyethylene, Polycarbophil, Carbopol, hydroxy-propyl-methyl-cellulose, carboxy-methyl-cellulose, hydroxy-propyl-cellulose, hydroxy-ethyl-cellulose, Guar rubber, alginates; drum-dried waxy maize starch (more commonly indicated with acronym DDWM).

In this solution the rifaximin in dissolved up to a concentration, preferably but not exclusively, between 0.5% and 30% by weight.

In order to make such a solution of the desired consistency and porosity, it is submitted to cycles of freezing and warming up (preferably but not exclusively in number between one and nine, preferably but not exclusively in an interval of temperature between −90° C. and +20° C.).

In alternative, in order to make such a solution of the desired solid consistency and porosity, it can be submitted to drying process (preferably but not exclusively at a temperature between 35° C. and 40° C.) or to the freezing-drying procedure like described by C. Callens, And Adrians, K. Dierckens, J. P. Remon on journal of the Controlled Release, volume 76 of year (2001), to page 83.

Equivalently, in order to make such a solution of the desired solid consistency and porosity, a divalent salt (preferably but not exclusively, calcium chloride) up to a concentration (preferably but not exclusively) of 2% by weight, can be dissolved in it.

Optionally, in association with the rifaximin, the solid-gel material can contain and delivery others drugs such as antibiotics and/or an anti-inflammatory and/or a pain-relief and/or anesthetic ones that could be useful for a better effect.

In the following it can be found a description that shows a practical, preferable but not exclusive, realization of the device for the delivery of rifaximin in the oral cavity.

Figure 2:
FIG. 2 is a cross-sectional view along the line of FIG. 1 with adhesive.
Figure 3:
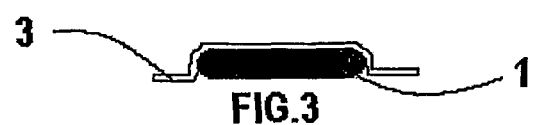
FIG. 3 is a cross-sectional view along the line of FIG. 1 as the film is applied to the external surface of a material containing a drug.
Figure 4:
FIG. 4 is a cross-sectional view along the line of FIG. 1 with a bi-adhesive film applied to the internal surface of a polymer material.

In the FIG. 1 it is shown the device in shape of film,

The FIG. 2 shows the section of the device following the line—of FIG. 1, when adhesive, put in 2, it is stirred homogenously inside the polymer material 1;

FIG. 3 shows the section of the device following the line—of FIG. 1, when the adhesive film, with or without holes, 3, it is applied to the external surface of the material containing the drug;

FIG. 4 shows the section of the device following the line—of FIG. 1, when a bi-adhesive film, with or without holes, 4, it is applied to the internal surface of the polymer material.

The way of application of the device, described in this invention, can happen by means of a simple pressure, in the place of interest, in order to let the adhesive attach to the gum or toot and to guarantee the effectiveness of the drug delivery.

The device can be placed directly in contact with the mucosa or other tissue of the oral cavity, and the adhesive element 3 (with or without holes) overlapping the material and going beyond the same, joins the surface of the neighboring gum (or other tissue) to guarantee its stability.

In an alternative way, the device can be placed directly in contact with the mucosa or other tissue of the oral cavity, with the bi-adhesive element, 4, between the mucosa, and the device itself.

Moreover, the rubber-like gel material can be tailored to the wanted shape and placed in a periodontal pocket between the periodontal tissue and the gum for the release of the rifaximin and, eventually, others antibiotics effective for the bacterial flora present in that place.

The rubber-like gel material can be also attached onto the surface of a catheter by dipping or coatings or by others conventional means to delivery rifaximin.

A further application of the device is its use in the rectum or in the vagina. This can be obtained by means of the same material, preferably but not exclusively, in cylindrical shape with a rounded off extremity (like a candle), with eventually, the mean for its extraction and recovery at the end of its use.

The invention claimed is:

1. A device for controlled local delivery of rifaximin to a mucosa of a body, the device comprising:
    rifaximin; and
    a bi-phasic material comprising a solid phase and a liquid phase, wherein the solid phase is an elastic polymeric matrix comprising polyvinylalcohol, and the liquid phase comprises water that fills up the pores of said polymeric matrix to form an interstitial solution, wherein the weight ratio between the water and the polymeric matrix is up to 10, and wherein the concentration of rifaximin dissolved in the interstitial solution is between 0.5% and 30% by weight,
    wherein the biphasic material enhances dissolution of rifaximin in the interstitial solution to deliver an efficacious concentration of rifaximin to the mucosa at a site where the device is placed, without permeation of rifaximin through the mucosa to form a systemic concentration of rifaximin, and to avoid the intense red color of rifaximin at the site where the device is placed.

2. The device of claim 1, wherein said polymeric matrix further comprises a polymer selected from the group consisting of polysaccharides, alkyl-cellulose, hydroxyalkyl-cellulose, and polyacrylates.

3. The device of claim 1, wherein said polymeric matrix further comprises an acrylic polymer.

4. The device of claim 3 comprising between 0.5 wt % and 30 wt % of rifaximin, 10 wt % of polyvinylalcohol and between 0.2 wt % and 20 wt % of acrylic polymer.

5. The device of claim 1, further comprising a bio-adhesive polymer.

6. The device of claim 5, wherein said bio-adhesive polymer is selected from the group consisting of hydroxypropylmethylcellulose, alginates, carboxymethylcellulose, hydroxyethylcellulose, and acrylic polymers.

7. The device of claim 5, wherein said bio-adhesive polymer is homogeneously mixed into the polymeric matrix.

8. The device of claim 5, wherein said bio-adhesive polymer is applied to the surface of the polymeric matrix.

9. The device of claim 1, wherein the device is in the form of a film.

10. The device of claim 1, further comprising an additional active agent selected from the group consisting of antibiotics, anti-inflammatory drug, pain relieving drug, anesthetic drug, and any combinations thereof.

11. A method for the delivery of rifaximin in the oral cavity that comprises applying the device of claim 5.

12. A process for preparation of a device according to claim 1 comprising the following steps:
    a) dissolving rifaximin and the polymeric matrix in water to prepare a solution; and
    b) adding a divalent salt to the solution of step a).

13. The process as claimed in claim 12, wherein said divalent salt is calcium chloride.

14. The process as claimed in claim 12, wherein said divalent salt is added at a concentration of up to 2 wt %.

15. The process as claimed in claim 12, wherein said solution of the step a) contains 10 wt % of polyvinylalcohol, between 0.2 wt % and 20 wt % of acrylic polymer and between 0.5 wt % and 30 wt % of rifaximin.

16. The device of claim 1, wherein the mucosa is in a body cavity selected from the group consisting of oral cavity, pharyngeal cavity, nasal cavity, rectum, and vagina.

\* \* \* \* \*